(12) United States Patent
Kim et al.

(10) Patent No.: US 8,314,405 B2
(45) Date of Patent: Nov. 20, 2012

(54) APPARATUS FOR MEASURING FLUORESCENCE LIFETIME

(75) Inventors: Dug Young Kim, Gwangju (KR); Sucbei Moon, Gwangju (KR); Dongsoo Lee, Gwangju (KR)

(73) Assignee: Gwangju Institute of Science and Technology, Gwangju (KR)

( * ) Notice: Subject to any disclaimer, the term of this patent is extended or adjusted under 35 U.S.C. 154(b) by 1071 days.

(21) Appl. No.: 12/252,313

(22) Filed: Oct. 15, 2008

(65) Prior Publication Data
US 2009/0095911 A1    Apr. 16, 2009

(30) Foreign Application Priority Data
Oct. 16, 2007 (KR) .................. 10-2007-0104132

(51) Int. Cl.
*G01T 1/10* (2006.01)
*G01N 21/61* (2006.01)
(52) U.S. Cl. ................... 250/458.1; 250/461.1
(58) Field of Classification Search ............. 250/363.01, 250/458.1, 459.1, 461.1, 461.2; 356/328, 356/318, 334
See application file for complete search history.

(56) References Cited

U.S. PATENT DOCUMENTS

| | | | | |
|---|---|---|---|---|
| 5,548,124 | A * | 8/1996 | Takeshima et al. | 250/458.1 |
| 5,955,737 | A * | 9/1999 | Hallidy et al. | 250/458.1 |
| 2004/0007675 | A1* | 1/2004 | Gillispie et al. | 250/458.1 |
| 2008/0265177 | A1* | 10/2008 | Connally et al. | 250/461.2 |

* cited by examiner

*Primary Examiner* — David Porta
*Assistant Examiner* — Faye Boosalis

(57) ABSTRACT

Disclosed is an apparatus for measuring a fluorescence lifetime. The apparatus for measuring the fluorescence lifetime comprises an excitation light generator that generates excitation light to be irradiated on a sample including fluorescence molecules; a fluorescence photon collecting unit that collects a plurality of fluorescence photons generated by irradiating the excitation light on the sample; a light sensor that converts the collected fluorescence photons into a fluorescence electrical signal; and a fluorescence lifetime signal processor that determines the fluorescence lifetime by calculating the average time of the fluorescence electrical signal with respect to a predetermined apparatus delay time. According to the above configuration, the present invention can accurately and precisely measure a fluorescence lifetime in a short measurement time by easy calculation.

17 Claims, 5 Drawing Sheets

APPARATUS FOR MEASURING FLUORESCENCE LIFETIME

BACKGROUND OF THE INVENTION

1. Technical Field

The present invention relates to an apparatus for measuring a fluorescence lifetime, and more specifically to an apparatus for precisely measuring a fluorescence lifetime that is an inherent optical characteristic of fluorescence materials in a short measurement time. This invention provides a means to acquire the fluorescence lifetime information for high-speed measurement applications such as a fluorescence lifetime imaging microscope that acquires an image of spatial distribution of the fluorescence lifetime for a fluorescent sample.

2. Related Art

A molecule can absorb an incident photon as a result of electronic transition from the ground state to a higher energy level when the molecule has an electronic state with the potential energy that matches to the energy of the incident photon. A fluorescence emission phenomenon is observed for a certain kind of molecules, which emit fluorescence photons by the excited electron returning back to the ground state. For fluorescent molecules, each molecule has a characteristic absorption wavelength and fluorescence emission wavelength. Meanwhile, the difference between those two wavelengths is called Stoke's shift and is typically on the order of tens of nanometers in wavelength. In other words, a fluorescence molecule absorbs a photon of excitation light and emits a photon of a slightly longer wavelength or a little less energy than that of the excitation photon. The fluorescence materials can be characterized and specified by the absorption wavelength and the emission wavelength of light. The fluorescence microscopy takes advantage of this specific characteristic of fluorescence materials by using optical filters that distinguish the fluorescence signals from the unwanted noisy excitation background.

The fluorescence microscope equips a light source that irradiates excitation light onto the microscope sample. The wavelength of the excitation light should match to the absorption wavelength of target fluorescent materials that reside in the microscope sample. By using an optical filter, the microscope selectively detects the intensity of the fluorescence signal at a wavelength longer than that of the excitation light.

Two kinds of photo-detectors can be utilized for the purpose: image sensors and single photo-detectors. Image sensors include films and solid-state array photo-detectors such as a charge-coupled device (CCD) and acquire the spatially distributed information of an image by a parallel manner at once. This methodology of image acquisition in microscopy is often called wide-field microscopy and is used for most of the existing conventional microscopes.

On the other hand, the image information is acquired by a scanning methodology. In scanning microscopy such as a confocal microscope, the signals of an image are acquired sequentially by a scan of the measurement point. Single photo-detectors such as a photo-multiplier tube (hereinafter, referred to as PMT) are used for the scanning microscopes.

The fluorescence microscope can be applied to obtain images by taking advantage of an intrinsic fluorescence property of a sample (auto-fluorescence). But it is mainly used to acquire an image of extrinsic fluorescence distribution in biological microscopy applications. Fluorescence dye molecules or fluorescent proteins are diffused and chemically bound to target molecules inside samples such as a cell or tissue. This process of sample preparation is often called labeling or staining. The labeled biological sample is highlighted at the parts stained with the extrinsic fluorescence molecules for a fluorescence microscope to acquire the distribution of a certain kind of the target molecules in the sample.

Most of the conventional fluorescence microscopes acquire image information based on intensity of fluorescence light. But advanced methods of forming images by collecting spectroscopic information other than the intensity of fluorescence are being recently developed. In particular, the information on the fluorescence lifetime is important in the advanced microscopy because it can provide more detailed information on the environments by which the fluorescence materials are surrounded.

Electrons in fluorescence molecules are excited by excitation light and then stay in the excited state for a while. Thereafter, the electrons in the excited state are transited to the ground state emitting a fluorescence photon. The temporal delay between the excitation and emission events for a photon is basically random but obeys a characteristic probability function given by the principle of quantum mechanics.

Before the excited electron being in the fluorescent state, the electron may stay in an intermediate state for a moment. But the excited electron usually relaxes to the fluorescent state almost immediately after being excited with only a few picoseconds for most of fluorescence molecules. This intermediate process is called relaxation of the excited electron. Neglecting this fast relaxation process, the photon emission probability is solely determined by the quantum-mechanical properties of the fluorescence state and the ground state. And each molecule has its own transition characteristic that determines the average time for which the electron stays in the fluorescent state, which is called the fluorescence lifetime.

The transition probability of electrons, that is, the generation probability of the fluorescence photons reaches a peak at the time point of the excitation, neglecting the ultra-fast relaxation process. Thereafter, the transition probability is characterized by an exponential decay curve. The time constant of the exponential decay curve is referred to as the fluorescence lifetime and can be measured by investigating the generation time of a plurality of fluorescence photons.

The fluorescence lifetime is regarded as a characteristic constant of each fluorescence molecule in the case of being isolated. However, the fluorescence lifetime can change according to the environment by which the fluorescence materials are surrounded when the environment provides an effective intermediate state through which the electron can pass. Various ions can provide electrons with such a non-fluorescent pathway to the ground state. Presence of such a competing pathway can decrease the fluorescence emission efficiency and the fluorescence lifetime as compared to the case of the absence.

Fluorescence molecules can play roles of molecular sensors of various ions such as oxygen, hydrogen, calcium or sodium ions, when decreases in the fluorescence efficiency or lifetime can be effectively detected. It is the principle of the fluorescence lifetime imaging microscopy (hereinafter, referred to as FLIM), which investigates the spatial concentration distribution of the above-mentioned ions using the information on the fluorescence lifetime in space. The same principle can be applied to a new class of microscopy technique: Föster resonance energy transfer (hereinafter, referred to as FRET) microscopy. In FRET microscopy, a fluorescence molecule of another kind is used to provide the excited electron with a new fluorescent pathway competing with its own internal pathway. The nanometric distance between the two molecules can be measured by detecting the change of the fluorescence lifetime.

Various image acquisition techniques of FLIM and FRET for wide-field microscopy have been developed by utilizing gated image intensifiers. The gated image intensifiers are the high-speed switchable version of image intensifiers that have fast gating or switching capabilities. They provide a way of measuring a short fluorescence lifetime by taking a series of images with varying temporal delays with respect to the moment of excitation. Because of the parallel signal acquisitions, this wide-field microscopy methodology of fluorescence lifetime measurement can make acquisition of a lifetime image completed within less than a few seconds. However, the scheme of fluorescence lifetime measurement for the wide-field microscopy can not be applied to high-resolution three-dimensional scanning microscopy such as a confocal microscopy due to the nature of parallel signal acquisitions.

On the other hand, the scanning microscopy including the confocal microscope and the multi-photon excitation fluorescence microscope provides better resolutions with depth-sectioning capabilities. This kind of microscopes performs a measurement on a spatial point at a time and scans the measurement point spatially, thereby sequentially obtaining the image information. Signal acquisition of the confocal microscope is performed selectively for a focus of an objective lens of the microscope. The image is constructed by the relative movement of the focus. The confocal microscope utilizes a spatial filter, such as a pinhole, that is placed at the confocal point after the objective lens and distinguishes the fluorescence signal of the objective focal region from the out-of-focus signals. The multi-photon excitation fluorescence microscope can naturally obtain the same effect without using a pinhole because the multi-photon absorption-excitation phenomenon occurs effectively at the focus having a high light intensity as a nonlinear process.

By utilizing a fluorescence lifetime measurement instrument, a scanning microscope can obtain FLIM images. There is little difference between an apparatus for measuring the fluorescence lifetime in the scanning FLIM microscopy and an apparatus for measuring the fluorescence lifetime in the time-resolved spectroscopy. The measurement of a fluorescence lifetime in the typical time-resolved spectroscopy mainly uses a time-correlated single photon counter (Hereinafter, referred to TCSPC) or a phase fluorometer. Those lifetime measurement instruments can be employed by a scanning microscope as a special photo-detector of optical signal sensing to implement a scanning FLIM microscope system.

The measurement of a fluorescence lifetime can be achieved by measuring a plurality of photons generated by a plurality of fluorescence molecules or a plurality of photons generated by exciting a fluorescence molecule many times as in the single-molecule spectroscopy. This is basically a process of analyzing a time-domain intensity of fluorescence that appears to be an exponential decay function. If an infinite number of fluorescence photons are collected and detected, the obtained time-domain fluorescence intensity will equal to the probability distribution function of fluorescence photon emission of the molecules in the case of impulse excitation. When a molecule is excited by a very short excitation pulse as an impulse excitation at t=0, the intensity of fluorescence light or the density of fluorescence photons $I_F(t)$ has the following distribution in time.

$$I_F(t)=I_0 e^{-t/\tau} u(t)$$

where $I_0$ represents an initial value of the function, $\tau$ represents the fluorescence lifetime, and $u(t)$ represents the step function of $u(t)=0$ when $t<0$ and $u(t)=1$ when $t \geq 0$. In other words, the fluorescence lifetime is the time required for the emission probability of the fluorescence photon to be reduced by a factor of 1/e after the moment of excitation. For organic fluorescence molecules used for biological or medical imaging applications, the lifetimes are typically between 0.1 ns and 5 ns.

The TCSPS detects a single-photon response owing to the high-gain photodetectors like a PMT or an avalanche photo diode (APD). As a photon counter, the TCSPC detects only a single photon at a time and counts the number of detected photons in measuring the detected time or arrival time of the photons. The arrival time of a single photon can precisely be measured by using a constant-fraction discriminator that detects the rising edge of the photo-electronic pulse of the single photon in time. The temporal precision of arrival time determination is even finer than the electronic response time of the photo-detector characterized by the full duration of the impulse response. Thus the TCSPC can provide better temporal resolutions so that it can accurately measure short lifetimes of a few hundreds of picoseconds.

A temporal histogram of fluorescence photon emission detection events is obtained by using the TCSPC photodetection instrument. The histogram shows the characteristic exponential decay function of fluorescence emission with a fine time resolution. In order to obtain a histogram of a good signal-to-noise ratio, more than thousands of photon counts should be detected by the TCSPC. Thereafter, the histogram is considered as the probability distribution function (PDF) of fluorescence emission. The fluorescence lifetime can be extracted from the histogram by various signal processing methods. The most popular method of signal analysis is the curve fitting method, in which the histogram is fitted by an exponential decay function that best matches to the histogram. An alternative analysis method is the mean delay method, in which the expected value of arrival time, that is, the time average of the measured histogram function is calculated. Because the mean temporal delay of an exponential decay function is equal to the lifetime, the fluorescence lifetime is calculated by finding the mean delay with respect to the initial time point of the decay.

Because of superior characteristics of the TCSPC in precision and accuracy of lifetime determination, the TCSPC is widely used in the time-resolved spectroscopy and the scanning FLIM microscopy. However, the TSCPC has a problem of a long measurement time, which is a fundamental problem in the single photon counting method. Since the TCSPC can count only a single photon for each measurement period, the intensity of fluorescence signal should be intentionally reduced so that the number of photons is less than one for each pulse. If more than two photons are sensed by the counter within the measurement period, in particular, if two photons are almost simultaneously arrived so that they cannot be divided into two distinct pulses, the counter detects only the value of the first arrived photon. As a result, the measured fluorescence lifetime is shorter than the actual value due to the signal loss.

Because of the "single photon condition", the measurement of a fluorescence lifetime in the TCSPC is completed only after the photon counting is performed many times by inputting a plurality of excitation light pulse. Also, the time interval between the excitation light pulses should be sufficiently longer than the fluorescence lifetime to be measured. If the time interval between the excitation light pulses is not sufficiently longer than the fluorescence lifetime, the decay waveforms of two adjacent fluorescence emissions may overlap, making it impossible to obtain an accurate value of the fluorescence lifetime. The pulse period of the excitation light should be, at least, five times longer than the fluorescence lifetime τ. Therefore, if a fluorescence lifetime to be measured is 5 ns, the frequency of the photon count will be lower than 40 MHz ($40 \times 10^6$ photons/sec) under the conditions that the excitation light pulse period is longer than 25 ns and one fluorescence photon is counted for each pulse period. Because the emission and measurement probability of a fluorescence photon has a random characteristic, the average number of photons detected for each period should be even smaller than one to ensure the single photon condition. The average number of photons per pulse period should be, at least, 1/10 to make the probability of multiple photons being detected less than 1/100 for an accurate analysis of a fluorescence lifetime. Thus the average frequency of photon counting should be lower than 4 MHz in this condition. And the number of counts required for a lifetime determination is larger than 100 to obtain a random error of less than 10% (<0.5 ns for a lifetime of 5 ns) in standard deviation. Therefore, the measurement rate can not exceed 40 kHz and the measurement period should be larger than 25 μs.

This property of a low measurement speed of the TCSPC limits the image acquisition speed of the scanning FLIM microscope that uses the TCSPC for fluorescence lifetime determination. The microscope image is usually composed of one million pixels. Since it takes longer than 25 μs to measure a fluorescence lifetime for a pixel, the time required to acquire a full image is longer than 25 seconds. Furthermore, a three-dimensional image consists of a plurality of two-dimensional images. Assuming 100 2D images are required for a 3D image, it takes longer than 2,500 seconds (~⅔ hour) to acquire the full signals. It is a serious obstacle in practical applications of the FLIM microscopy, especially for continuous observations of live organisms.

A reliable high-speed fluorescence lifetime measurement scheme is desired for the multi-dimensional FLIM microscopy application. In order to fulfill the speed requirement, a single lifetime determination should be completed within less than a few microseconds. The accuracy and precision should be good enough to reliably determine a short lifetime below 1 ns.

SUMMARY OF THE INVENTION

It is a technical problem of the present invention to provide an apparatus for measuring a fluorescence lifetime that is capable of accurately and precisely measuring a fluorescence lifetime at a high measurement speed through an easy calculation and suitable for a fluorescence lifetime imaging microscope acquiring an image based on a spatial distribution of the measured fluorescence lifetime.

In order to solve the technical problem, the present invention presents an apparatus for measuring a fluorescence lifetime that comprises: an excitation light generator that generates excitation light in a pulsed form to be irradiated on a sample including fluorescence molecules; a fluorescence photon collecting unit that collects a plurality of fluorescence photons generated by irradiating the excitation light on the sample; a light sensor that converts the fluorescence photons into a fluorescence electrical signal in a pulsed form; and a fluorescence lifetime signal processor that determines the fluorescence lifetime by calculating the time average or the average time of the fluorescence electrical signal with respect to a predetermined apparatus delay time.

The predetermined apparatus delay time may be predetermined by the fluorescence lifetime signal processor calculating the time average or the average time of a reference electrical signal that is obtained by the light sensor converting the excitation light.

The predetermined apparatus delay time may be predetermined by the fluorescence lifetime signal processor calculating the time average or the average time of a fluorescence electrical signal for a sample of known fluorescence lifetime and taking a value for the predetermined apparatus delay time that makes the fluorescence lifetime measured by the apparatus equal to the known fluorescence lifetime of the sample.

The average time of the reference electrical signal may be previously obtained through the light sensor and the fluorescence lifetime signal processor, followed by the calculation of the average time.

The excitation light generator may include an objective lens that condenses the excitation light and irradiates the condensed excitation light on the sample.

The fluorescence photon collecting unit may include: a fluorescence photon collecting lens that collects the generated fluorescence photons; and an excitation light removing filter for preventing the excitation light from being delivered to the light sensor.

The reference electrical signal may be generated by converting the excitation light in the light sensor, the excitation light being generated in a state of the sample and the excitation light removing filter being removed.

The fluorescence lifetime signal processor may include: a signal measuring unit that measures the fluorescence electrical signal and the reference electrical signal delivered from the light sensor; and a fluorescence lifetime calculator that calculates the average time of the fluorescence electrical signal and the average time of the reference electrical signal and determines the difference therebetween as the fluorescence lifetime.

The apparatus for measuring the fluorescence lifetime further comprises a light splitter and an excitation light reflector, wherein the excitation light is separated into the sample and the excitation light reflector through the light splitter and the reference electrical signal is an electrical signal obtained by the separated excitation light being reflected by the excitation light reflector and the light sensor converting the reflected excitation light.

The apparatus for measuring the fluorescence lifetime further comprises an optical fiber delay unit that gives a temporal delay of the light delivery and is placed between either the light splitter and the sample or the light splitter and the excitation light reflector.

The excitation light generator may include: an excitation light source that generates the excitation light in a pulsed form; and an objective lens that condenses the generated excitation light and irradiates the condensed excitation light on the sample.

The fluorescence photon collecting unit may include a fluorescence photon collecting lens that collects the fluorescence photons generated from the sample.

The light sensor may convert the excitation light delivered from the excitation light reflector and the fluorescence photons delivered from the sample into the fluorescence electrical signal and the reference electrical signal, respectively.

The fluorescence lifetime signal processor may includes: a signal measuring unit that measures the fluorescence electrical signal and the reference electrical signal delivered from the light sensor; and a fluorescence lifetime calculator that calculates the average time of the fluorescence electrical signal and the average time of the reference electrical signal and determines the difference therebetween as the fluorescence lifetime.

DESCRIPTION OF EXEMPLARY EMBODIMENT

Figure 1:
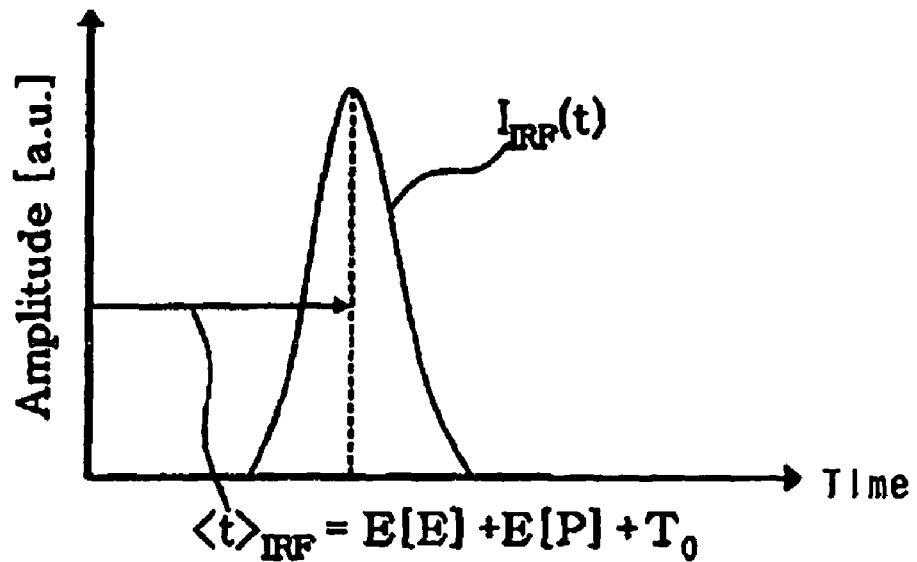
FIG. 1 is a pair of schematic graphs for explaining a measurement of a fluorescence lifetime according to the present invention.
Figure 1:
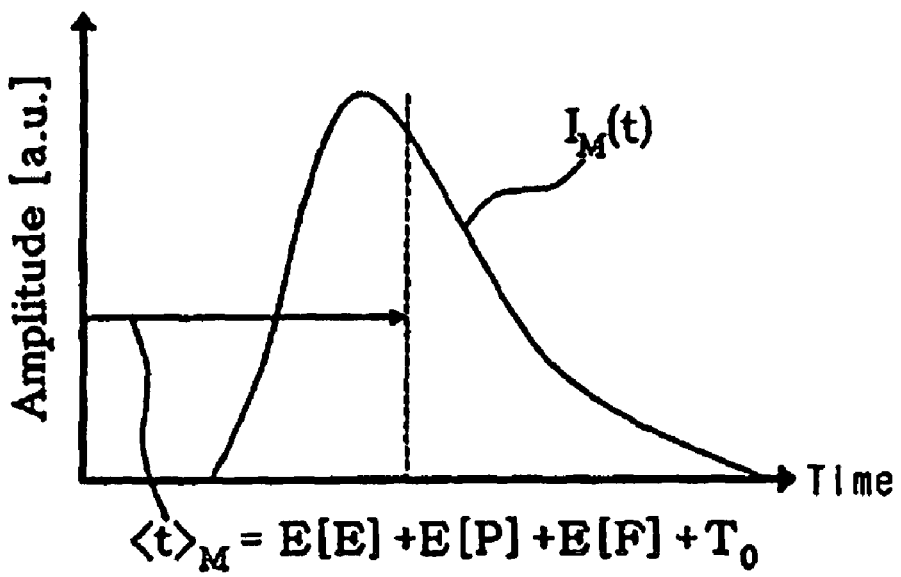

Hereinafter, exemplary embodiments of the present invention will be described with reference to the accompanying drawings. Like components are denoted by like reference numerals in the following description and throughout the accompanying drawings and therefore, the duplicated description thereof will not be repeated. Also, the concrete description of the known function or configuration will not be repeated in the description of the present invention when making the subject matter of the present invention unnecessarily obscure.

The principle of fluorescence lifetime measurement according to the present invention will be described at first, prior to the explanation of the exemplary embodiments of the present invention.

The most intuitive method for measuring a fluorescence lifetime is the method that inputs excitation light of a short pulse form into a sample and measures a time waveform of emitted fluorescence intensity with a high-speed light sensor. A pulse-type laser may be used as a source of the excitation light having a short pulse width. The intensity of fluorescence is usually very low and therefore, a light sensor of a high signal amplification gain such as a photo-multiplier tube (PMT) or an avalanche photo diode (APD) is highly preferred. The electric response time of such a light sensor is relatively long. As a result, it is difficult for the light sensor to measure a short fluorescence lifetime of less than 1 ns accurately. This is because the waveform measured by the light sensor is given by a convolution of an exponential decay function of fluorescence and a characteristic response function of the light sensor called as an impulse response function as in the following equation.

$$I_M(t) = I_E(t) \otimes I_F(t+T_0) \otimes I_P(t) \quad \text{[Equation 1]}$$

where $\otimes$ represents the convolution operation, $I_M(t)$ represents the measured analog current or voltage waveform obtained by the light sensor, $I_E(t)$ represents the time-domain shape of the excitation light pulse, $I_F(t)$ represents the fluorescence intensity given as an exponential decay function, $I_P(t)$ represents the impulse response function of the light sensor, and $T_0$ represents the delay time of light delivery from the excitation light source to the light sensor via the fluorescence emission of the sample. The delay time can be determined as a characteristic value of the measurement system that is not relevant to the fluorescence phenomenon. Then, $I_E(t) \otimes I_P(t)$ is an instrumental response function (hereinafter, referred to as IRF) and is denoted by $I_{IRF}(t)$. $I_{IRF}(t)$ is a characteristic function of the measurement system that is not involved with the fluorescence phenomenon. In practice, the IRF can be measured by obtaining the measurement system response for a sample of an extremely short fluorescence lifetime or by removing a sample and making the excitation light detected by the light sensor directly so that the analog waveform detected by the light sensor is the convolution of $I_E(t)$ and $I_{IRF}(t)$.

Setting the origin of the time coordinate at the moment of the excitation pulse generation, the detected waveform is shifted by the delay time $T_0$. For the detected waveform being equal to the fluorescence decay function, the IRF should be an impulse-like function of an extremely short pulse width. In most cases, however, the width of the IRF is not sufficiently small due to the finite response time of the light sensor. The pulse width of the IRF is determined by the light sensor when the pulse width of the excitation light is even smaller than that of the response function of the light sensor. For a practical high-gain light sensor such as a PMT or an APD, the width of the IRF is usually larger than 1 ns in full width at half maxima (FWHM). Therefore, the accuracy degradation caused by the finite width of the IRF can not be neglected even in the case of relatively long fluorescence lifetimes of ~5 ns.

The Fourier-transformation deconvolution is a conventional method of removing the contribution of the IRF in the measured analog waveform. This method of signal processing Fourier-transforms the measured analog waveform $I_M(t)$ and the IRF waveform $I_{IRF}(t)$ into their Fourier conjugate functions, $I_M(f)$ and $I_{IRF}(f)$ in the frequency domain. Note that those functions in the frequency domain are complex functions and can be represented by their magnitudes and phases in general. If the inverse Fourier transformation is performed after calculating $I_M(f)$ divided by $I_{IRF}(f)$, $I_F(t)$ will solely remain by the mathematical characteristics of the Fourier transformation and the convolution. It is because the convolution relation is transformed into an algebraic multiplication relation in the frequency domain.

A method of directly calculating the fluorescence lifetime in the frequency domain without performing the inverse Fourier transformation can be considered. This is the principle of the phase fluorometer. The fluorescence lifetime in the frequency domain can be expressed as a function of the frequency-domain phase or as a function of the frequency-domain magnitude of $I_F(f)$ under the assumption of an exponential decay of fluorescence. The method of calculating a fluorescence lifetime using only the phase component in the frequency domain is as follows. If a difference between the phase components of the complex function $I_F(f)$ and the phase component of $I_{IRF}(f)$ is denoted by $\theta(f)$, the fluorescence lifetime $T_{ph}(f)$ is as follows.

$$T_{ph}(f) = \tan(\theta(f))/2\pi f$$

And the fluorescence lifetime is obtained by averaging $T_{ph}(f)$ for the frequency range of high signal-to-noise ratios.

Therefore, measured results of analog waveforms are transformed into the frequency domain by the Fourier transformation, the contribution of the IRF will represented by an algebraic relation, such as a simple multiplication (for the magnitude) or an addition (for the phase), making it possible to remove the contribution of the IRF with ease.

However, these methods rely on a computationally heavy process of the Fourier transformation. Although a high-speed algorithm, such as a fast Fourier transformation (FFT), is developed as an efficient discrete Fourier transformation algorithm for the digital computer, it is still a process that requires lots of computation powers for real-time operation. This problem can be avoided by an analog phase measurement apparatus based on an electric mixer in the conventional phase fluorometer. However, this kind of methods based on analog circuits may suffer from the errors caused by the inaccurate analog signal processing. And the measurement speed is limited by the finite bandwidth of the analog electrical apparatus. Also, the accuracy of the measurement results may be deteriorated by the photo-bleaching effect because the continuous decrease of the fluorescence intensity due to photo-bleaching results in the measured phase error for the analog mixer.

In order to perform high-speed measurement of a fluorescence lifetime, which is one of the technical problems of the present invention, the fluorescence lifetime should be determined by processing an analog electrical signal generated by a plurality of fluorescence photons, not by a response according to a single photon as in the TCSPC as mentioned in the above. The contribution of the limited response speed of the light sensor, that is, the distortion of the measured intensity waveform to the actual intensity should be considered and compensated. In order to obtain a good accuracy of the measured fluorescence lifetime, which is another technical problem of the present invention, the fluorescence lifetime should be determined by the signal process having an attribute removing the contribution of the IRF with ease. This should be implemented by using an easy and high-speed calculation method unlike the Fourier transformation-based algorithm.

The operation of removing the contribution of the IRF may generally be called the deconvolution process in that the pulsed fluorescence electrical signal measured by the light sensor is the exponential decay curve of the fluorescence emission that is convolved with the IRF and this convolution characteristic is eliminated by this deconvolution process. Thus the present invention is presenting a new domain of deconvolution process in which the convolution relation changes to a simple algebraic relation to be calculated with ease.

Determination of a fluorescence lifetime according to the present invention is performed by a subtraction operation of the time averages of the measured analog pulsed waveform of fluorescence that is called the fluorescence electric signal and the measured IRF that is called the reference electric signal. Thus obtaining the time averages can be understood as a transformation process for deconvolution.

For both the measured electric signals of the fluorescence electric signal and the reference electric signal, a pulsed electrical signal generated by an infinite number of fluorescence photons can be interpreted as a probability distribution function (hereinafter, referred to as PDF) of arrival times of the photo-electrons, which are the electrons originating from the photo-detection process in the light sensor. In practice, a pulsed electric signal detected by the light sensor is composed of a finite number of photo-electrons, originating from a finite number of fluorescence photons, also originating from a finite number of excitation photons. Thus a detected electric signal in practice has a random characteristic obeying the PDF in the average characteristic.

For a detected photo-electronic signal of the lifetime measurement system, each electron is generated by a signal of a photon and arrives at the signal processor after experiencing a set of random processes in time to be described below. The full arrival time for the electron arriving at the signal processor is a sum of several random time delays and constant time delays. And each random process of a random time delay has its own characteristic PDF. By the principle of the statistics, a sum of individual random variables corresponds to the convolution of the corresponding PDFs. Therefore, the following equation corresponds to the above-mentioned Equation 1.

$$M=E+(F+T_0)+P \Leftrightarrow I_M(t)=I_E(t) \otimes I_F(t+T_0) I_P(t) \quad \text{[Equation 2]}$$

where M, E, F, and P are the random time variables of $I_M(t)$, $I_E(t)$, $I_F(t)$, and $I_P(t)$, respectively, which are considered as the corresponding PDFs of the random variables. $T_0$ is a fixed variable determined as a fixed delay time by the optical path of the measurement apparatus. Specifically, M represents a full arrival time from the excitation pulse generation to the signal acquisition at the fluorescence lifetime signal processor. E represents a random absorption-excitation delay time due to the non-zero pulse width of the excitation pulse. P represents a random photo-electron feeding delay time due to the non-zero pulse width of the impulse response function of the light sensor. And F represents a random fluorescence emission delay time due to the non-zero lifetime of fluorescence photon generation.

Hereinafter, the expected value of a random time variable T is denoted by E[T]. When T has a PDF of A(t) as a function of the time coordinate variable t, E[T] can be denoted like the below.

$$E[T] = \langle t \rangle = \frac{\int_{T_1}^{T_1} A(t)\,dt}{\int_{T_1}^{T_2} A(t)\,dt} \quad \text{[Equation 3]}$$

where A(t) is bounded by $T_1$ and $T_2$. Optionally, E[T] can be denoted by <t> as a mean time. In principle, functions like an exponential decay function are not bounded at the tail and should be integrated for the full range to the positive infinite. However, an approximate finite integration up to five times a characteristic time constant from the beginning point of the exponential decay gives a sufficiently accurate result of a small error of 0.7%. Therefore, there is little difference between the finite integration of a sufficiently large integration interval and the integration of the infinite integration interval for most cases.

The operation of obtaining an expected value is a linear operation so that an expected value of a summation of random variables is a summation of the expected values of the random variables. Thus the following equation is derived for the time averages from Equation 2.

$$M=E+(F+T_0)+P \Leftrightarrow E[M]=E[E]+E[F]+E[P]+T_0 \quad \text{[Equation 4]}$$

Equation 4 means that the average delay time E[M] for the fluorescence electrical signal waveform reaching the fluorescence lifetime signal processor to be described below is equal to a sum of IRF delay, which is $E[E+P]+T_0=E[E]+E[P]+T_0$, and the fluorescence emission delay E[F]. Since the characteristic time constant τ of an exponential decay curve is equal to the average delay time value of the curve (τ=E[F]), the fluorescence lifetime τ is finally represented by τ=E[M]−{E[E]+E[P]+$T_0$}.

Hereinafter, the time delay of {E[E]+E[P]+$T_0$} is called the apparatus delay time, which is a characteristic value of the measurement apparatus and should be calibrated for determination of the fluorescence lifetime. The apparatus delay time is also understood as the average delay time of the delayed IRF that can be measured by obtaining the reference electric signal for a virtually or actually zero lifetime for the lifetime measurement system apparatus, that is, E(M) for E(F)=0. Therefore, the fluorescence lifetime is a value subtracting the average delay time of the measured reference electric signal from the average delay time of the measured fluorescence electric signal.

A fluorescence lifetime is determined by subtracting the apparatus delay time from the average time of the fluorescence electrical signal according to the present invention. The apparatus delay time can be obtained by taking the average time of the reference electrical signal with ease. However, the apparatus delay time can be calibrated by other methods. For example, it is possible to determine a value of the apparatus delay time $T_a$ that makes a measured fluorescence lifetime of $\tau = E[M] - T_a$ equal to the known fluorescence lifetime of a sample. The fluorescence lifetime of the sample may be measured by an fluorescence lifetime measurement apparatus such as a TCSPC apparatus prior to the fluorescence lifetime measurement of the present invention. Or the apparatus delay time can be determined by measuring or estimating the time delays of all the parts of the measurement apparatus individually and taking the summation of the time delays as the apparatus delay time. But the calibration method using the reference electrical signal is recommendable due to a good accuracy and easiness in determining the apparatus delay time.

The numerical computation for the fluorescence lifetime measurement according to the present invention may performed by an analog computing circuit composed of an analog integrator or a digital computing unit such as a digital signal processor (DSP) in principle. The digital signal processing usually produces more accurate results and can be performed after the electrical signal being digitized by an analog-to-digital converter. In the digital case, the electrical signal being digitized should be band-limited by the Nyquist's sampling theorem. Because of the processing speed limitation of the digital computing unit, the sampling rate of the analog-to-digital converter needs to be carefully optimized and a suitable anti-aliasing electric low-pass filter may be necessary. Note that the effect of such a low-pass filter can be understood as a part of the light sensor and can not hamper an accurate measurement of a fluorescence lifetime according to Equation 4.

The measurement method of a fluorescence lifetime according to the present invention may look similar to a TCSPC method that uses an alternative signal analysis scheme of the average delay time, which is described in the section of the related art above. However, the average delay time in the TCSPC method is utilized as a kind of curve fitting method to analyze the shape of a measured exponential decay curve. And this TCSPC method does not take advantage of the deconvolution characteristic of the average delay time and, furthermore, only measures a single photon within a pulsed excitation period. In contrast, the present invention gives a measurement method to acquire the information of a plurality of fluorescence photons detected in an excitation period. The present invention is also characterized as a non-TCSPC method that enhances the measurement time resolution by using the deconvolution property of the average delay time instead of taking advantage of the scheme of the TCSPC.

FIG. 1 is a pair of schematic graphs for explaining a measurement of a fluorescence lifetime according to the present invention. The upper graph shows a schematic plot of a reference electric signal. And the lower graph shows a schematic plot of a fluorescence signal. Referring to FIG. 1, $<t>_{IRF}$ represents the average delay time of the delayed IRF that is measured as a reference electric signal. $<t>_M$ represents the average delay time of the fluorescence electric signal that contains the information of the fluorescence delay function of E[F]. If the measurement apparatus had an optical or electric path of the reference electric signal measurement which is different from that of the fluorescence electric signal measurement, the path length difference should be compensated by shifting the time coordinate. In other words, the origins of the time coordinates should be the same with each other to eliminate the bias. E[F], that is, the fluorescence lifetime $\tau$ can be obtained by taking the difference between the average times of the two waveforms by the principle of the statistics.

Figure 2:
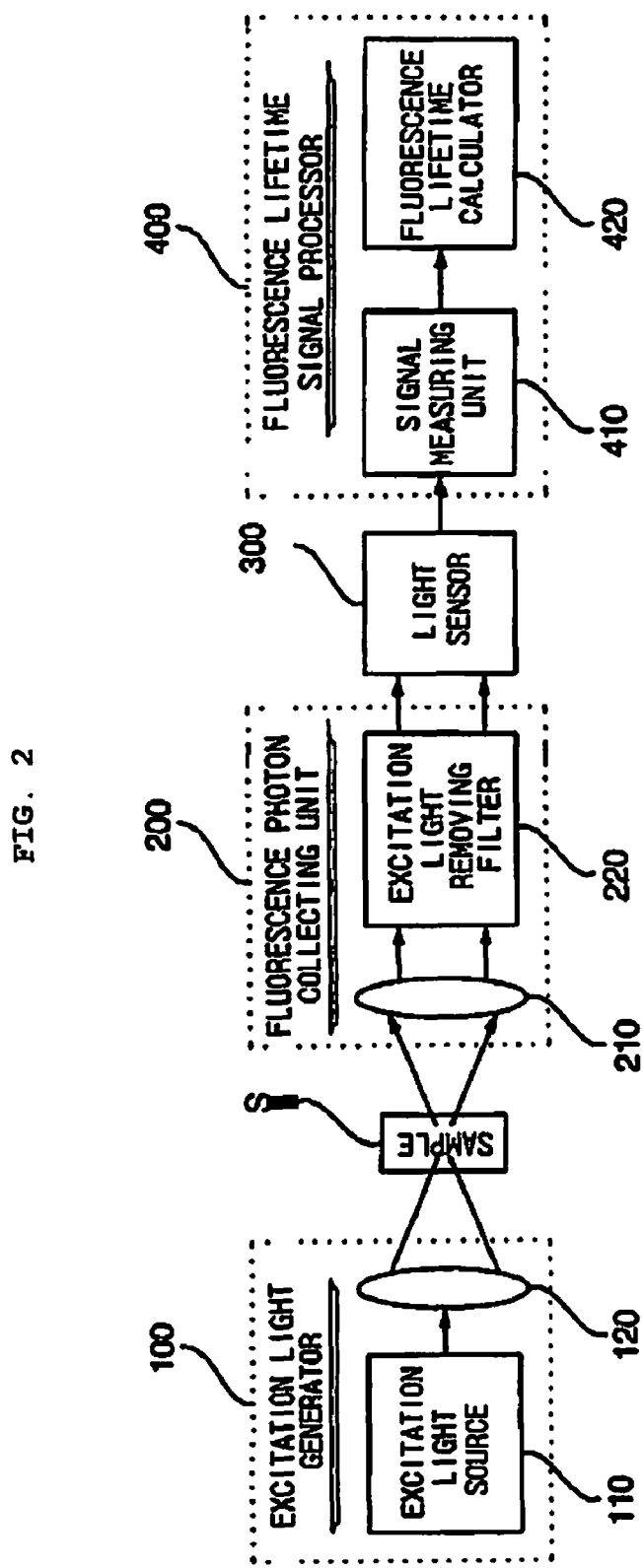
FIG. 2 is a block view of an apparatus for measuring a fluorescence lifetime according to one embodiment of the present invention.

FIG. 2 is a block view of the apparatus for measuring a fluorescence lifetime according to one embodiment of the present invention. Referring to FIG. 2, an excitation light generator 100, which is a module that generates excitation light to be irradiated on a sample S, includes an excitation light source 110 generating the excitation light in a pulse form and an objective lens 120 that condenses the generated excitation light and irradiates it on the sample S.

A fluorescence photon collecting unit 200, which is a module collecting a plurality of fluorescence photons generated by the excitation light being irradiated on the sample S, includes a fluorescence photon collecting lens 210 that collects the plurality of fluorescence photons generated by the sample and an excitation light removing filter 220 that prevents the excitation light from being collected and delivered to a light sensor 300 to be described below. In an optional structure, the objective lens 120 can play a role of the fluorescence photon collecting lens 210 when the backward propagating fluorescence photons are selectively delivered to the excitation light removing filter 220 by using a dichroic mirror or a beam splitter.

The light sensor 300 converts the fluorescence photon that is collected by the fluorescence light collecting lens 210 and selectively passed by the excitation light removing filter 220, into photo-electrons and optionally amplifies the photo-electrons by an electron multiplication process, resulting in an electrical signal (referred to as a fluorescence electrical signal). By removing the sample S and the excitation light removing filter 220, the light sensor generates an electrical signal of the instrumental response function (referred to as a reference electrical signal) without changing the other measurement conditions of measuring fluorescence electrical signal. As the light sensor, for example, the photo-multiplier tube (PMT) or the avalanche photo diode (APD) can be used.

A fluorescence signal processor 400, which is a module numerically calculating the fluorescence lifetime by using the electrical signals obtained by the light sensor 300, includes a signal measuring unit 410 that measures the electrical signal to be processed numerically and a fluorescence lifetime calculator 420 calculating the fluorescence lifetime based the measured waveforms. Herein, the signal measuring unit 410 may use, for example, an analog-to-digital converter and the fluorescence lifetime calculator may use, for example, a digital computer. Herein, the signal measuring unit may contain an electrical low-pass filter.

A fluorescence lifetime calculator 420 calculates the fluorescence lifetime using a difference between the average time of the fluorescence electrical signal and the average time of the reference electrical signal. The fluorescence electrical signal corresponds to the above-mentioned $I_M(t)$, and the reference electrical signal corresponds to the above-mentioned apparatus response function $I_{IRF}(t)$.

In the present embodiment, the average time of the reference electrical signal needs to be measured separately to the measurement of the fluorescence electrical signal. For example, it may be measured prior to the determination of the average time of the fluorescence electrical signal and the value of the average time of the reference electrical signal is stored in the memory of the measurement apparatus and can be loaded to the fluorescence lifetime calculator 420 when calculating the difference between those two average times. The average time of the reference electrical signal is measured by allowing the excitation light to reach the light sensor 300 without an interaction with the sample S and the excitation light removing filter 220 and then measuring the electrical signal delivered from the light sensor 300 by the signal measuring unit 410 and obtaining the average time of the measured electrical signal in the fluorescence lifetime calculator 420.

For simplicity, Hereinafter, the time coordinate t in denoting electrical signals and average times is assumed to be shifted by a certain constant amount so that the electrical signals are bounded by the origin (t=0) on the rising edge side. In the case of using a digital computing unit for digital signal processing, the fluorescence lifetime calculator 420 may use the interpolation techniques such as a cubic spline interpolation to enhance the accuracy of the digital integration.

The average time $E_1[t]$ of the fluorescence electrical signal can be calculated in the fluorescence lifetime calculator 420 using the following equation.

$$E_1[t] = \frac{\int_0^T tA(t)\,dt}{\int_0^T A(t)\,dt} \qquad \text{[Equation 5]}$$

where A(t) represents the fluorescence electrical signal and T, which is an integral period, may be set to a specific value according to the accuracy of the measurement of the fluorescence lifetime.

Also, the average time $E_2[t]$ of the reference electrical signal can be calculated in the fluorescence lifetime calculator 420 using the following equation.

$$E_2[t] = \frac{\int_0^T tB(t)\,dt}{\int_0^T B(t)\,dt} \qquad \text{[Equation 6]}$$

where B(t) represents the reference electrical signal and T is the same value as the integral period in the equation.

The fluorescence lifetime calculator 420 determines the fluorescence lifetime by taking the difference of $E_1-E_2$.

As an optional signal processing and calculation method, an iterative calculation algorithm of the average time can be used to minimize a deterministic error caused by amplitude offset of the signal measuring unit 410 or the dark-current noise of the light sensor 300. Such a direct-current error (DC error) may be generated by many noise or error sources of the light sensor and the signal measuring unit. And this DC error makes the obtained average time deviate from the actual value. The effect of the DC error can be neutralized by setting the center point of the integration interval in Equation 5 or Equation 6 at the average time point calculated by the integration. Because the average time is unknown before an integration calculation, this integration interval setting should be performed by an iterative algorithm in which an average time is re-calculated by using the average time calculated before the re-calculation step. In other words, an average time is repeatedly calculated by the average time calculated in the previous step being fed for optimizing the integration interval step by step.

Figure 3:
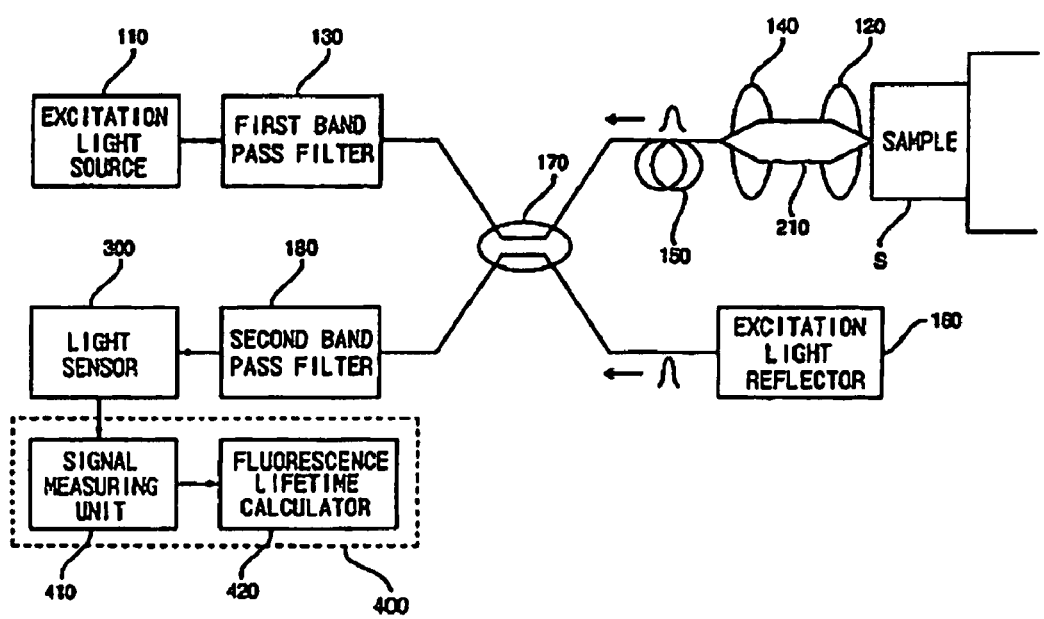
FIG. 3 is a block view of an apparatus for measuring a fluorescence lifetime according to another embodiment of the present invention.

FIG. 3 is a block view of an apparatus for measuring a fluorescence lifetime according to another embodiment of the present invention. In this embodiment, the reference electrical signal is measured simultaneously with the fluorescence electrical signal by intentionally delaying one of the two electrical signals. In the embodiment of FIG. 2, the change of the measurement conditions may be produced and degrade the accuracy of the measured lifetime because the determination of the average time of the reference electrical signal is performed separately to that of the fluorescence electrical signal in time.

Referring to FIG. 3, the excitation light generator generating the excitation light to be irradiated on the sample including the fluorescence molecules includes the excitation light source 110 that generates the excitation light in a pulse form, a first band pass filter 130 that selectively passes the excitation light in a specific band, an excitation light collimating lens 140 that collimates the excitation light, and the objective lens 120 that condenses and irradiates the condensed excitation light on the sample S.

The focal points of the excitation light collimating lens 140 and the objective lens 120 are in the confocal geometry. And the two lenses also play a role of collecting and delivering the fluorescence photons backward to the light sensor 300 as well as a role of delivering and condensing the excitation light forward to the sample.

In this embodiment, optical beam delivery of both the excitation light and the fluorescence light is performed by optical fibers for implementation simplicity. A fiber coupler 170 separates the excitation light passed by the band filter 130 into two paths. In one of the two paths, the excitation light is delivered to the sample S through the excitation light collimating lens 140 and the objective lens 120. In the other path, the excitation light is delivered to an excitation light reflector 160 and is reflected back to the fiber coupler. For the backward propagating light, the fiber coupler acts as a light combiner, which combines the fluorescence light from the excitation light collimating lens 140 and the excitation light reflected by the excitation light reflector 160. The fiber coupler 170 may be replaced by an optical splitter or a dichroic mirror that selectively reflects or transmits the excitation light and the fluorescence light according to the wavelength of the light as a sort of an optical filter. Using a dichroic mirror for the purpose may enhance the delivery efficiency at the sacrifice of the implementation complexity.

The excitation light delivered to the sample S is subjected to a predetermined time delay by passing through an optical fiber delay unit 150. The optical fiber delay unit 150 may be placed between the fiber coupler 170 and the excitation light reflector 160 optionally. In any case, the predetermined time delay should be applied to one of the two paths for the pulsed fluorescence electrical signal and the pulsed reference electrical signal to be measured separately in time.

A second band pass filter 180 is placed at the port of the fiber coupler in which the excitation light reflected by the excitation light reflector and the fluorescence light are combined together. The second band pass filter effectively passes the fluorescence light with a low loss but effectively attenuates the excitation light to be of a low intensity comparable to that of the fluorescence light to avoid the saturation of the light sensor.

The light sensor 300 converts the excitation light passed by the band pass filter 180 that is fed by the excitation light reflector 160 and a plurality of fluorescence photons from the sample to the reference electrical signal and the fluorescence electrical signal, respectively. Because of the predetermined time delay of the optical fiber delay unit 150, those two pulsed electrical signals are separated by a temporal interval. Accordingly, the light sensor 300 generates the two electrical signals which are time-division multiplexed. The fluorescence electrical signal is converted before the reference electrical signal is converted. Thus the predetermined time delay of the optical fiber delay unit 150 should be determined so that the two pulses of the fluorescence electrical signal and the reference electrical signal are not overlapped and have a sufficient temporal gap between them at the output port of the light sensor.

Also, the fluorescence lifetime signal processor 400 includes a signal measuring unit 410 that measures the electrical signals, and a fluorescence lifetime calculator 420 that calculates the fluorescence lifetime based on the measured results. The fluorescence lifetime calculator 420 calculates the average time of the fluorescence electrical signal according to above-mentioned Equation 5 and the average time of the reference electrical signal according to above-mentioned Equation 6. And it determines the difference therebetween as the measured fluorescence lifetime.

The operation details of the signal measuring unit 410 and the fluorescence lifetime calculator 420 are the same with those of the previous embodiment explained by FIG. 2 except for that the time coordinate t for either the fluorescence electrical signal or the reference electrical signal is shifted by the above-mentioned predetermined time delay to compensate the path length difference between those two signals before the calculation of the average times. The predetermined time delay can be calibrated by measuring the average times of a fluorescence electrical signal and a reference electrical signal for a sample of virtually zero lifetime, and taking the difference therebetween as the predetermined time delay to be compensated.

Figure 4:
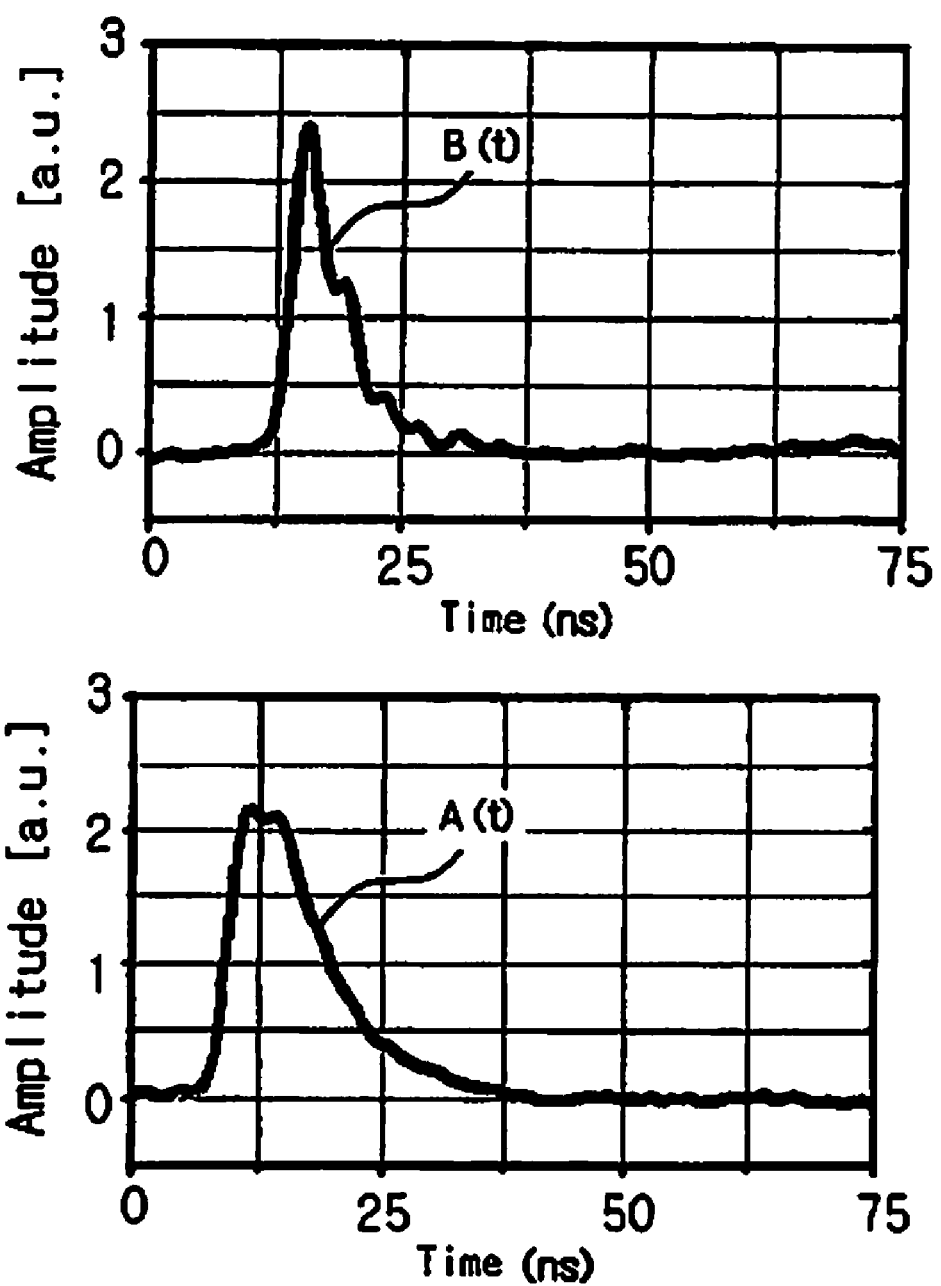
FIG. 4 is a pair of graphs showing an example of a pair of waveforms of a fluorescence electrical signal and a reference electrical signal measured by a signal measuring unit 410 according to the embodiment of FIG. 3.

FIG. 4 is a pair of graphs showing an example of a pair of waveforms of a fluorescence electrical signal and a reference electrical signal measured by a signal measuring unit 410 according to the embodiment of FIG. 3. Referring to FIG. 4, the waveform in the lower graph A(t) represents the fluorescence electrical signal and the waveform in the upper graph B(t) represents the reference electrical signal. The time coordinate of each waveform was shifted according to the signal processing method explained in the above. In this measurement, a fluorescent dye called Alexa Fluor 633 diluted by distilled water was used as a sample. A pulsed laser diode operating at a wavelength of 650 nm was used for the excitation light source 110. An oscilloscope capable of sampling 2 billions of data points with 8-bit depth was used as the signal measuring unit 410. The fluorescence lifetime calculator 420 calculated the average time of the respective waveforms measured as shown in FIG. 4 and could determine the difference therebetween as the fluorescence lifetime. The fluorescence lifetime was measured to be 3.2 ns.

Figure 5:
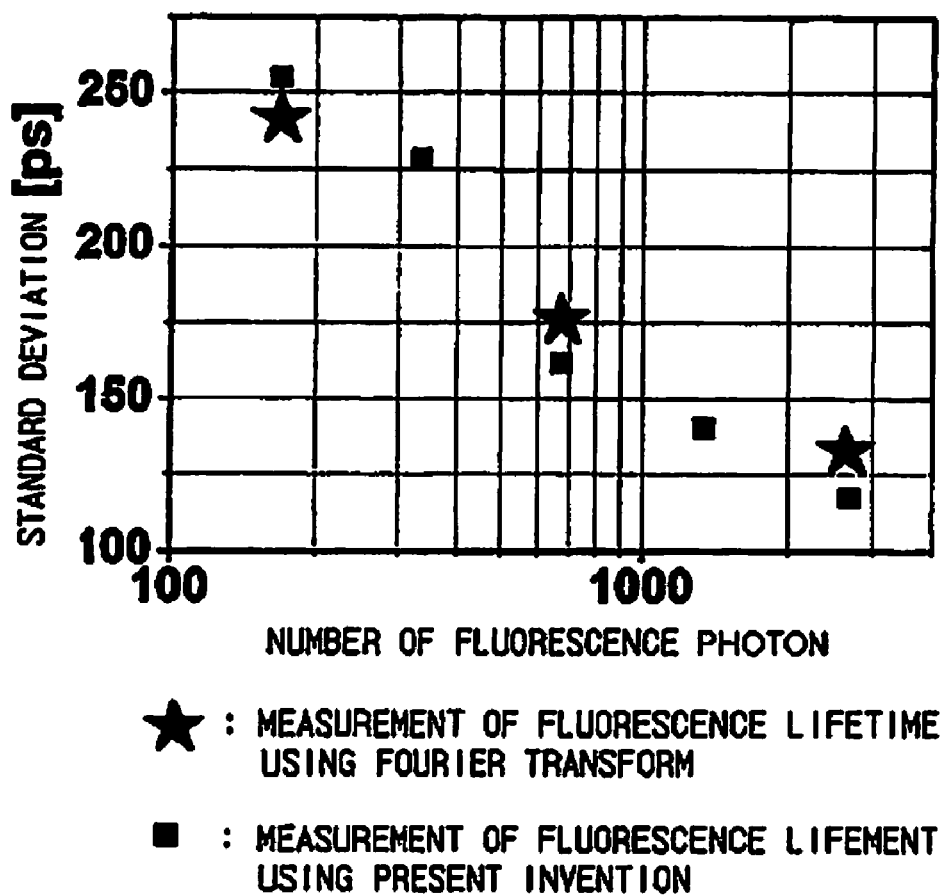
FIG. 5 is a view showing the comparison results of the standard deviations of the fluorescence lifetimes measured according to the present invention and those of the fluorescence lifetimes measured using the Fourier transform method.

FIG. 5 is a view showing the comparison results of the standard deviations of the fluorescence lifetimes measured according to the present invention and those of the fluorescence lifetimes measured using the Fourier transform method. The comparison was performed for the experimental condition of FIG. 4. In the Fourier transform method, the measured waveforms of a fluorescence electrical signal and a reference electrical signal are Fourier-transformed and the fluorescence lifetime is determined by calculating the phase difference in the frequency domain. The fluorescence lifetime measured according to the present invention was 3.27 ns and the fluorescence lifetime measured using the Fourier transform method was 3.22 ns. As can be appreciated therefrom, the fluorescence lifetime measured according to the present invention and the fluorescence lifetime measured according to the conventional frequency-domain method that is equivalent to that of the conventional phase fluorometer well match to each other. This result shows the accuracy of the fluorescence lifetime measurement according to the present invention is as good as the conventional method.

The precision of a fluorescence lifetime measurement method is evaluated by the amount of the random error in determining a fluorescence lifetime. In the statistical analysis, it is evaluated by the standard deviation of measured lifetimes for repeated measurements. In general, the precision is given as a function of the number of detected photons involved with a measurement. Thus the precision should be compared in regard to the number of detected photons. As shown in FIG. 5, it can also be appreciated from the measured results of the standard deviations of the fluorescence lifetimes that the precision performance of the fluorescence lifetime measurement method according to the present invention is as good as the conventional method of the Fourier transform method.

As described above, the apparatus and method for measuring a fluorescence lifetime according to the present invention can measure a fluorescence lifetime with good accuracy and precision owing to the deconvolution characteristic, in which the contribution of the instrumental response function is removed effectively, in a short measurement time in comparison to the conventional TCSPS method, through a relatively simple calculation in comparison to the conventional Fourier transform method. Determination of the average delay time and the apparatus delay time can be performed by a simple integral operation, but this can be performed by a simple analog circuit as well as a digital computation.

The apparatus and method for measuring a fluorescence lifetime according to the present invention have a very small calculation quantity as compared to the calculation quantity of the deconvolution method through the Fourier transformation that should perform the integral operations many times, making it possible to obtain a processing speed much faster than the deconvolution method. For example, in the case of a discrete Fourier transform, the required number of algebraic operations for a signal having N data points is $N^2$ in number of addition and multiplication operation pairs. The fast Fourier transform (FFT) of an efficient discrete Fourier transform algorithm requires the number of operation pairs of $N \log_2 N$ for the signal. However, the number of operation pairs in the apparatus and method for measuring a fluorescence lifetime according to the present invention is only 4N for the signal. Thus the calculation quantity according to the present invention is much smaller than the deconvolution method through the Fourier conversion.

Therefore, when the apparatus and method for measuring a fluorescence lifetime according to the present invention is applied to the fluorescence lifetime imaging microscope, it is possible to acquire an image in a short time of a few seconds so that images can be obtained in real time.

On the other hand, a part of the embodiments of the present invention as described above can be prepared as a program executable in a computer and can be implemented by a general-use digital computer running program using a recording medium readable by the computer. The recording medium readable by the computer includes a magnetic storage medium (for example, ROM, floppy disk, hard disk, etc.), an optical reading medium (for example, CD-ROM, DVD, etc.), and a storage medium such as a carrier wave (for example, transmission through an internet).

It will be apparent to those skilled in the field of the art that various modifications and changes may be made without departing from the scope and spirit of the present invention. Therefore, it should be understood that the above embodiments are not limitative, but illustrative in all the aspects. The scope of the present invention is defined by the appended claims rather than by the description preceding them, and therefore all changes and modifications that fall within metes and bounds of the claims, or equivalents of such metes and bounds are therefore intended to be embraced by the claims.

What is claimed is:

1. An apparatus for measuring a fluorescence lifetime, the apparatus comprising:
   an excitation light generator configured to generate excitation light in a pulse form to be irradiated on a sample including fluorescence molecules;
   a fluorescence photon collecting unit configured to collect a plurality of fluorescence photons generated by irradiating the excitation light on the sample;
   a light sensor configured to convert the fluorescence photons into a fluorescence electrical signal in a pulse form; and
   a fluorescence lifetime signal processor configured to determine the fluorescence lifetime by calculating a time average or an average time of the fluorescence electrical signal with respect to a predetermined apparatus delay time.

2. The apparatus of claim 1, wherein the predetermined apparatus delay time is determined by the fluorescence lifetime signal processor by calculating the time average or the average time of a reference electrical signal that is obtained by the light sensor converting the excitation light.

3. The apparatus of claim 2, wherein the fluorescence lifetime signal processor calculates the average time of the reference electrical signal, followed by the calculation of the average time of the fluorescence electrical signal.

4. The apparatus of claim 3, wherein the excitation light generator includes:
   an objective lens configured to condense the excitation light and irradiate the condensed excitation light on the sample.

5. The apparatus of claim 3, wherein the fluorescence photon collecting unit includes:
   a fluorescence photon collecting lens configured to collect the generated fluorescence photons; and
   an excitation light removing filter configured to prevent the excitation light from being delivered to the light sensor.

6. The apparatus of claim 5, wherein the reference electrical signal is generated by converting the excitation light in the light sensor after the sample and the excitation light removing filter are removed.

7. The apparatus of claim 3, wherein the fluorescence lifetime signal processor includes:
   a signal measuring unit configured to measure the fluorescence electrical signal and the reference electrical signal delivered from the light sensor; and
   a fluorescence lifetime calculator configured to calculate the average time of the fluorescence electrical signal and the average time of the reference electrical signal and determine the difference therebetween as the fluorescence lifetime.

8. The apparatus of claim 2, further comprising a light splitter and an excitation light reflector,
   wherein the light splitter configured to separate the excitation light and provide the separated excitation light to the sample and the excitation light reflector, respectively,
   wherein the excitation light reflector is configured to reflect the separated excitation light provided to the excitation light reflector, and
   wherein the light sensor is configured to generate the reference electrical signal by converting the separated excitation light reflected by the excitation light reflector.

9. The apparatus of claim 8, further comprising an optical fiber delay unit configured to apply a temporal delay to the separated excitation light, the optical fiber delay unit being disposed between the light splitter and the sample or between the light splitter and the excitation light reflector.

10. The apparatus of claim 8, wherein the excitation light generator includes:
    an excitation light source configured to generate the excitation light in a pulse form;
    an objective lens configured to condense the generated excitation light and irradiate the condensed excitation light on the sample.

11. The apparatus of claim 8, wherein the fluorescence photon collecting unit includes:
    a fluorescence photon collecting lens configured to collect the fluorescence photons generated from the sample.

12. The apparatus of claim 11, wherein the light sensor converts the separated excitation light reflected by the excitation light reflector into the reference electrical signal, and
    wherein the light sensor converts the fluorescence photons delivered from the sample into the fluorescence electrical signal.

13. The apparatus of claim 12, wherein the fluorescence lifetime signal processor includes:
    a signal measuring unit configured to measure the fluorescence electrical signal and the reference electrical signal delivered from the light sensor; and
    a fluorescence lifetime calculator configured to calculate the average time of the fluorescence electrical signal and the average time of the reference electrical signal and determines the difference therebetween as the fluorescence lifetime.

14. The apparatus of claim 1, wherein the fluorescence lifetime signal processor determines the predetermined apparatus delay time by calculating the time average or the average time of a fluorescence electrical signal of a sample having a known fluorescence lifetime and taking a value for the predetermined apparatus delay time that makes the fluorescence lifetime measured by the apparatus equal to the known fluorescence lifetime of the sample.

15. The apparatus of claim 2, wherein the reference electrical signal is denoted by B(t), and
    wherein the average time of the reference electrical signal denoted by $E_2$ is calculated using the following equation, $$E_2[t] = \frac{\int_0^T tB(t)\,dt}{\int_0^T B(t)\,dt}.$$

16. The apparatus of claim 1, wherein the fluorescence electrical signal is denoted by A(t), and
    wherein the average time of the fluorescence electrical signal denoted by $E_1$ is calculated using the following equation, $$E_1[t] = \frac{\int_0^T tA(t)\,dt}{\int_0^T A(t)\,dt}.$$

17. The apparatus of claim 1, wherein the predetermined apparatus delay time is calculated by the fluorescence lifetime signal processor using the time average or the average time of a fluorescence electrical signal of a sample having a known fluorescence lifetime, and the known fluorescence lifetime.

* * * * *